US009456752B2

(12) United States Patent  
Zeien

(10) Patent No.: US 9,456,752 B2  
(45) Date of Patent: Oct. 4, 2016

(54) FULL-FIELD THREE-DIMENSIONAL SURFACE MEASUREMENT

(71) Applicant: Aperture Diagnostics Ltd., Cutchogue, NY (US)

(72) Inventor: Robert Zeien, Cutchogue, NY (US)

(73) Assignee: APERTURE DIAGNOSTICS LTD., Cutchogue, NY (US)

( * ) Notice: Subject to any disclaimer, the term of this patent is extended or adjusted under 35 U.S.C. 154(b) by 458 days.

(21) Appl. No.: 13/830,477

(22) Filed: Mar. 14, 2013

(65) Prior Publication Data

US 2014/0276093 A1    Sep. 18, 2014

(51) Int. Cl.
*A61B 1/005*   (2006.01)
*A61B 1/07*    (2006.01)
*A61B 5/00*    (2006.01)
(Continued)

(52) U.S. Cl.
CPC ............. *A61B 5/0077* (2013.01); *A61B 1/005* (2013.01); *A61B 1/041* (2013.01); *A61B 1/07* (2013.01); *A61B 1/00016* (2013.01); *A61B 1/00032* (2013.01); *A61B 5/0073* (2013.01); *A61B 5/0084* (2013.01)

(58) Field of Classification Search
CPC  A61B 5/0073; A61B 5/0093; A61B 5/0077; A61B 1/00016; A61B 5/0084; A61B 1/005; A61B 1/041; A61B 1/07; A61B 1/00032; G01B 11/25
See application file for complete search history.

(56) References Cited

U.S. PATENT DOCUMENTS 5,016,173 A * 5/1991 Kenet ................. A61B 5/0059
382/128

5,581,352 A    12/1996  Zeien
5,587,832 A    12/1996  Krause
(Continued)

FOREIGN PATENT DOCUMENTS

WO    2011/027127 A2    3/2011

OTHER PUBLICATIONS

United States Patent and Trademark Office, International Search Report and Written Opinion/ISA in International patent application No. PCT/US2014/023285, mailed May 30, 2014, 12 pages.

(Continued)

*Primary Examiner* — Long V Le
*Assistant Examiner* — Don N Ho

(57) ABSTRACT

Embodiments of the present invention may be used to perform measurement of surfaces, such as external and internal surfaces of the human body, in full-field and in 3-D. Embodiments of the present invention may include an electromagnetic radiation source, which may be configured to project electromagnetic radiation onto a surface. The electromagnetic radiation source may be configured to project the electromagnetic radiation in a pattern corresponding to a spatial signal modulation algorithm. The electromagnetic radiation source may also be configured to project the electromagnetic radiation at a frequency suitable for transmission through the media in which the radiation is projected. An image sensor may be configured to capture image data representing the projected pattern. An image-processing module may be configured to receive the captured image data from the image sensor and to calculate a full-field, 3-D representation of the surface using the captured image data and the spatial signal modulation algorithm. A display device may be configured to display the full-field, 3-D representation of the surface.

6 Claims, 3 Drawing Sheets

(51) Int. Cl.
  *A61B 1/04* (2006.01)
  *A61B 1/00* (2006.01)

(56) References Cited

U.S. PATENT DOCUMENTS

| | | | |
|---|---|---|---|
| 5,615,003 A * | 3/1997 | Hermary | G01B 11/245 250/559.23 |
| 5,784,098 A | 7/1998 | Shoji et al. | |
| 5,847,832 A * | 12/1998 | Liskow | A61B 5/0064 356/605 |
| 6,115,058 A | 9/2000 | Omori et al. | |
| 6,178,346 B1 | 1/2001 | Amundson et al. | |
| 6,332,087 B1 | 12/2001 | Svenson et al. | |
| 6,364,831 B1 | 4/2002 | Crowley | |
| 6,503,195 B1 | 1/2003 | Keller et al. | |
| 6,579,285 B2 | 6/2003 | Sinfosky | |
| 6,695,779 B2 | 2/2004 | Sauer et al. | |
| 6,832,984 B2 * | 12/2004 | Stelzer et al. | 600/106 |
| 7,385,708 B2 | 6/2008 | Ackerman et al. | |
| 7,492,398 B1 | 2/2009 | Norita et al. | |
| 7,728,868 B2 | 6/2010 | Razzaque et al. | |
| 7,734,061 B2 | 6/2010 | Breed et al. | |
| 7,742,232 B2 | 6/2010 | Cho et al. | |
| 7,747,067 B2 | 6/2010 | Popescu et al. | |
| 7,751,694 B2 | 7/2010 | Cho et al. | |
| 7,812,968 B2 | 10/2010 | Bendall et al. | |
| 7,821,649 B2 | 10/2010 | Bendall et al. | |
| 7,846,107 B2 | 12/2010 | Hoffman et al. | |
| 8,094,322 B2 | 1/2012 | Mayer et al. | |
| 8,105,233 B2 | 1/2012 | Abou El Kheir | |
| 8,123,722 B2 | 2/2012 | Chang et al. | |
| 8,235,985 B2 | 8/2012 | Saadat et al. | |
| 8,419,613 B2 | 4/2013 | Saadat et al. | |
| 8,422,030 B2 * | 4/2013 | Bendall | G01B 11/25 356/447 |
| 8,900,219 B2 | 12/2014 | Sinofsky et al. | |
| 9,254,103 B2 * | 2/2016 | Krishnaswamy | A61B 5/7257 |
| 2003/0174208 A1 * | 9/2003 | Glukhovsky et al. | 348/131 |
| 2004/0133085 A1 * | 7/2004 | Hall | G01N 21/49 600/320 |
| 2005/0168735 A1 | 8/2005 | Boppart et al. | |
| 2009/0118622 A1 * | 5/2009 | Durkin | A61B 5/0073 600/473 |
| 2009/0259102 A1 | 10/2009 | Koninckx et al. | |
| 2010/0141829 A1 | 6/2010 | Jalali et al. | |
| 2010/0160904 A1 | 6/2010 | McMillan et al. | |
| 2011/0057930 A1 | 3/2011 | Keller et al. | |
| 2011/0205552 A1 | 8/2011 | Bendall et al. | |
| 2011/0242285 A1 | 10/2011 | Byren | |
| 2012/0029829 A1 | 2/2012 | Li et al. | |
| 2012/0035434 A1 | 2/2012 | Ferren et al. | |

OTHER PUBLICATIONS

Evans, J.L., et al., Accurate Three-Dimensional Reconstruction of Intravascular Ultrasound Data, Circulation (American Heart Association, Inc.), 93, pp. 567-576 (1996).

Gorthi, S.S., et al., Fringe Projection Techniques: Whither we are? Optics and Lasers in Engineering, 48(2), pp. 133-140 (2010).
Takeda, M., et al., Fourier Transform Profilometry for the Automatic Measurement of 3-D Object Shapes, Applied Optics, vol. 22, No. 24, pp. 3977-3982 (Dec. 1983).
IVUS Imaging Products Overview, Volcano Precision Guided Therapy, www.volcanocorp.com/products/ivus-imaging, 2012, 1 page.
Eagle Eye Platinum RX Digital IVUS Catheter, Volcano Precision Guided Therapy, product brochure, printed 2012, 4 pages.
Goodwin, J., A Capsule Camera Instead of a Colonoscopy, Health, May 10, 2011, 2 pages.
Maier-Hein et al., "Optical Techniques for 3D Surface Reconstruction in Computer-Assisted Laparoscopic Surgery," Medical Image Analysis 17, pp. 974-996, available May 3, 2013 (online <URL:// isit.u-clermont1.fr/~ab/Publications/Maier-Hein_etal_MIA13. pdf>).
Toennies et al., "Swallowable Medical Devices for Diagnosis and Surgery: the State of the Art," Proc. IMechE vol. 224 Part C: J. Mechanical Engineering Science, pp. 1397-1414, Dec. 9, 2009 (online <URL: https://ww.iris.sssup.it/retrieve/handle/11382/ 304585/994/JMESToennis_Webster.pdf>).
United States Patent and Trademark Office, International Search Report and Written Opinion/ISA in International patent application No. PCT/US2015/044636, mailed Mar. 21, 2016, 11 pages.
Barrera, F., et al., "Optical and Spectroscopic Properties of Human Whole Blood and Plasma with and without Y2O3 and Nd3+: Y2O3 Nanoparticles," Lasers Med Sci, 8 pages (Feb. 2013).
Cardiac Procedures and Surgeries At-A-Glance, American Heart Association/American Stroke Association, 4 pages, 2012.
Grundfest, W., et al., "Real-Time Percutaneous Optical Imaging of Anatomical Structures in the Heart Through Blood Using a Catheter-Based Infrared Imaging System," Seminars in Thoracic and Cardiovascular Surgery, 19:336-341 (2007).
Honda, Y., et al., "Frontiers in Intravascular Imaging Technologies," Circulation, 117:2024-2037 (2008).
Knight, B., et al., "Direct imaging of Transvenous Radiofrequency Cardiac Ablation Using a Steerable Fiberoptic Infrared Endoscope," Heart Rhythm, 2:1116-21 (2005).
Lundqvist, C.B., et al., "The Use of Imaging for Electrophysiological and Devices Procedures: A Report from the First European Heart Rhythm Association Policy Conference, Jointly Organized with the European Association of Cardiovascular Imaging (EACVI), the Council of Cardiovascular Imaging and the European Society of Cardiac Radiology," Europace, 15:927-936 (2013).
Mozaffarian, D., et al., "Heart Disease and Stroke Statistics—2015 Update: A Report from the American Heart Association." Circulation, 131:e29-e322, e535 (2014).
Roger, V., et al., "Heart Disease and Stroke Statistics—2012 Update: A Report from the American Heart Association," Circulation, 125:e2-e220, e1002 (2011).
Roggan, A., et al., "Optical Properties of Circulating Human Blood," Part of the SPIE Conference on Optical Diagnostics of Biological Fluids III, SPIE vol. 3252, pp. 70-82 (1998).

* cited by examiner

100

200

300

400

500

600

700

FULL-FIELD THREE-DIMENSIONAL SURFACE MEASUREMENT

BACKGROUND

Accurate three-dimensional maps of external and internal human body surfaces are necessary for many medical procedures. For example, external body surfaces may need to be scanned for facial reconstructive surgery or the fitting of prosthetics. Internal body surfaces may need to be mapped for various endoscopic or catheter-based procedures, such as virtual biopsy, stenting, ablation, bronchoscopy, esophogastrodenoscopy, laparoscopy, colonoscopy, cyctoscopy, or arthroscopy. Further, some internal procedures may take place in gaseous media, such as a bronchoscopy, and others may take place in liquid media, such as arthroscopy or cardiovascular visualization.

Current techniques for three-dimensional scanning external and internal body surfaces have many drawbacks. Laser-based scanning, such as a laser line scan, typically requires a patient to remain motionless, with even minor movements affecting the accuracy of the scan. A typical laser scan may require a patient to sit still for ten to fifteen seconds while many two-dimensional slices are gathered. The two-dimensional slices are later recompiled into a three-dimensional representation of a surface. Movement during this time period by the patient, including respiration, tremors, or muscle reflexes, can negatively impact the accuracy of the scan. Further, laser scanning equipment itself may introduce unwanted vibration into the system due to the inherent movement of the laser.

Commonly used techniques for internal organ measurements suffer from similar induced errors, these methods include: computed tomography (CT), optical coherence tomography (OCT), magnetic resonance imaging (MRI), and various ultra-sound approaches (US and IVUS).

Thus, a need exists for three-dimensional surface measurement techniques that may be performed quickly and may eliminate inaccuracies introduced by patients and equipment.

DETAILED DESCRIPTION

The present invention relates to real-time, full-field, three-dimensional ("3-D") surface replication. Embodiments of the present invention may be used to perform measurement of surfaces, such as external and internal surfaces of the human body, in full-field and in 3-D. Full-field may refer to the ability of a device's sensor to capture and compute 3-D information of an entire scene containing an object being measured, for example. Real-time may refer to use of sufficiently fast sensor exposures or frame-rates to minimize or eliminate perceptible target surface motion, for example.

Embodiments of the present invention may include an electromagnetic radiation source, which may be configured to project electromagnetic radiation onto a surface. The electromagnetic radiation source may be configured to project the electromagnetic radiation in a pattern corresponding to a spatial signal modulation algorithm. The electromagnetic radiation source may also be configured to project the electromagnetic radiation at a frequency suitable for transmission through the media in which the radiation is projected. An image sensor may be configured to capture image data representing the projected pattern. An image-processing module may be configured to receive the captured image data from the image sensor and to calculate a full-field, 3-D representation of the surface using the captured image data and the spatial signal modulation algorithm. A display device may be configured to display the full-field, 3-D representation of the surface.

Embodiments of the present invention may be further integrated into a probe, diagnostic or therapeutic catheter, endoscope, or a capsule to allow full-field, 3-D surface replication on internal surfaces of the human body. Such a device may be internally or externally guided, steerable or propelled in order to be advanced to, or navigated through cavities or the cardiovascular system.

Figure 1:
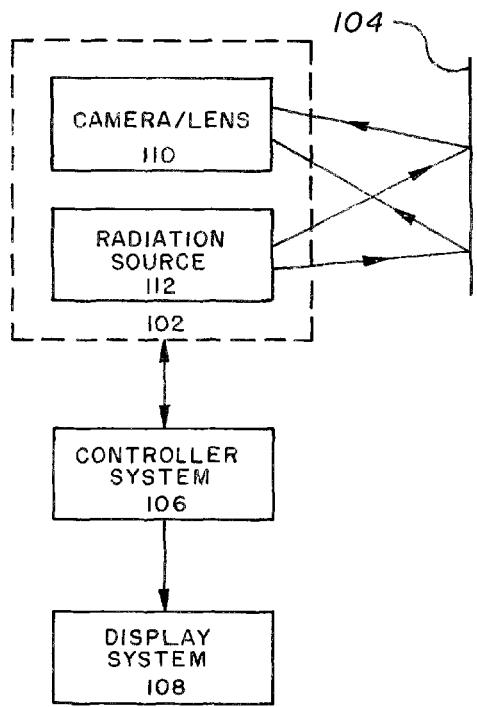
FIG. 1 illustrates an embodiment of the present invention.

FIG. 1 illustrates a real-time, full-field, 3-D surface replication system 100 according to embodiments of the present invention. System 100 may include a measurement package 102, a target surface 104, a controller system 106, and a display system 108. System 100 may implement the spatial signal modulation (SSM) techniques described in U.S. Pat. No. 5,581,352 filed on Feb. 27, 1995, the entirety of which is hereby incorporated by reference, to reproduce instant, quantifiable 3-D maps of external and internal surfaces of the human body.

Measurement package 102 may include a camera device 110 and a radiation source 112. The radiation source 112 may be fabricated by placing a slide or grating (not shown) with a desired pattern between a radiation emitting device and a lens (not shown). The camera device 110 may be a device capable of capturing image data reflected from the target surface 104 (e.g., a charge-coupled device (CCD) camera).

Controller system 106 (or image processing module) may include a processor or state machine capable of receiving image data captured by the camera device 110 and processing the data to calculate a full-field, 3-D representation of the target surface 104. Such a machine may include, for example, any suitable processing platform, computing platform, computing device, processing device, computing system, processing system, computer, processor, or the like, and may be implemented using any suitable combination of hardware and/or software.

Display system 108 may include a display device (liquid crystal display device, light emitting diode display device, etc.) to receive the full-field, 3-D representation of target surface 104 from the controller system 106 and display the digital representation of the surface 104 to be analyzed by a user.

Figure 2:
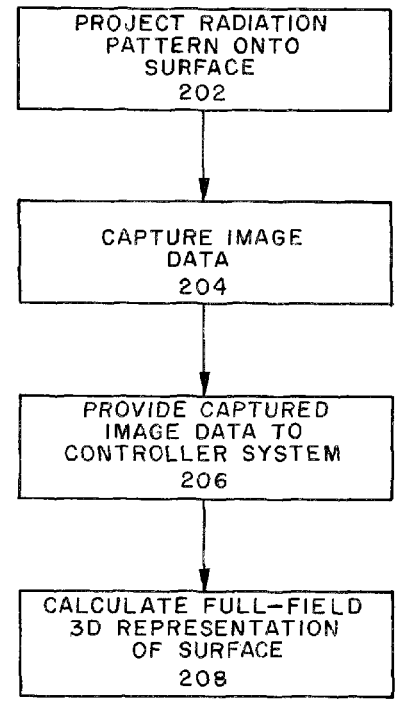
FIG. 2 illustrates a logic flow according to an embodiment of the present invention.

FIG. 2 is a logic flow 200 of an operation of the replication system 100 of FIG. 1 according to embodiments of the present invention. During operation, radiation source 112 may project a pattern of electromagnetic radiation, according to a spatial signal modulation algorithm, onto a target surface 104 (step 202). The pattern may take the appearance of parallel bands of electromagnetic radiation, for example. According to embodiments of the present invention, the carrier frequency of the projected spatial radiation signals may depend on the media the signals are propagating through. For example, human blood is some 2,500 times more transparent at certain infrared frequencies versus shorter wavelengths in the visible blue range. It is also not possible to use electromagnetic radiation to "see" an object if the wavelength of the radiation used is larger than the object. Thus, the emitter carrier frequency may be chosen based upon one or more characteristics (particle size, color, quantity of particles, etc.) of a media (air, blood, mucus, urine, etc.) adjacent to a target surface.

The spatial signals may reflect from the target surface 104 back to the camera device 110. The camera device 110 may capture the reflected spatial signals, which are changed/modulated by interaction with the surface 104 (step 204). The captured reflection images of the distorted projections contain spatially encoded 3-D surface information. Data representing the reflected (and distorted) spatial signals may be transmitted to the controller system 106 for processing (step 206).

Controller system 106 may include an image processing module and may use existing information regarding various signal parameters to isolate the content of the reflected spatial signal that contains the 3-D shape information. The shape information may be used to mathematically reconstruct the 3-D shape of target surface 104 (step 208). Controller system 106 may transmit digital data corresponding to the calculated representation of the surface 104 to the display system 108 to display a digital image representing a 3-D view of the surface 104.

Figure 3:
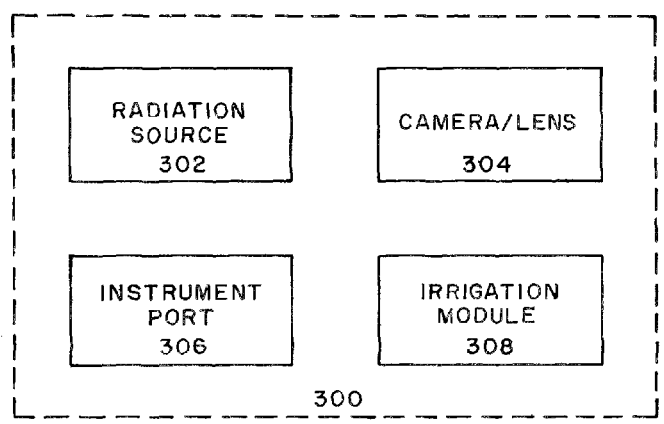
FIG. 3 illustrates a measurement package according to an embodiment of the present invention.

FIG. 3 illustrates a measurement package 300 according to embodiments of the present invention. Measurement package 300 may include a radiation source 302, a camera/lens device 304, an instrument port 306, and an irrigation module 308. Radiation source 302 and camera/lens device 304 (which are similar to radiation source 112 and camera device 110 in FIG. 1, respectively) are used to implement the SSM techniques described above.

Instrument port 306 may be a hollow tube that permits insertion of a wide array of surgical devices that may be interchanged during a procedure to fit the current needs of a physician. The irrigation module 308 may include a channel which introduces an inert fluid (e.g., saline) under pressure to clear debris off of the exterior of the camera/lens 304 during a procedure. Instrument port 306 and irrigation module 308 are optional features of measurement package 300.

Measurement package 300 may be implemented in a system (similar to system 100 of FIG. 1) to project radiation patterns with specific frequencies onto a surface, capture distorted reflections of the radiation pattern, and process the distorted reflections to facilitate analysis by an array of mathematical processes to reconstruct a 3-D shape of the surface. Embodiments of the present invention may integrate variations of measurement package 300 into medical devices to generate 3-D representations of various surfaces. For example, embodiments of the present invention may be used to generate 3-D representations of external human surfaces (e.g., faces, hands, feet, etc.). Embodiments of the present invention may also be used to generate 3-D representations of internal human surfaces (e.g., heart chambers, lungs, intestines, etc.).

Figure 4A:
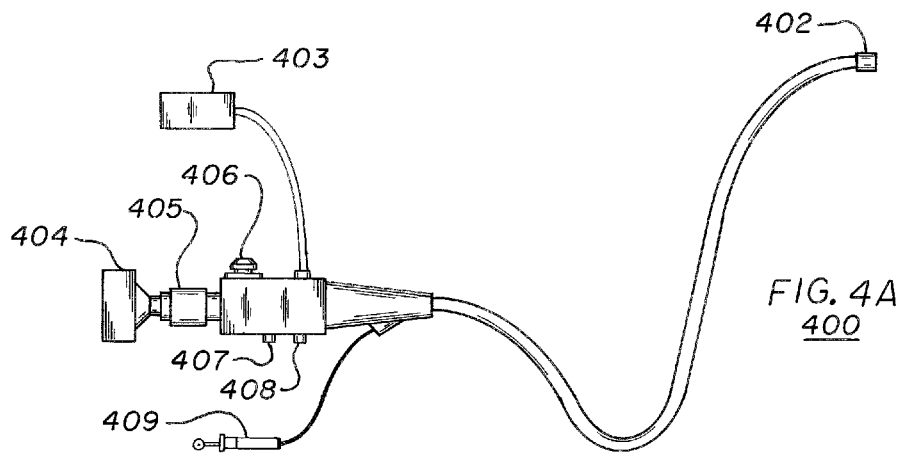
FIG. 4A illustrates an endoscope according to an embodiment of the present invention.
Figure 4B:
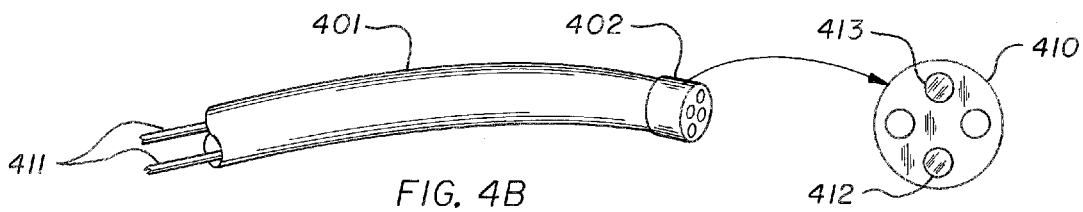
FIG. 4B illustrates an endoscope according to an embodiment of the present invention.
Figure 4C:
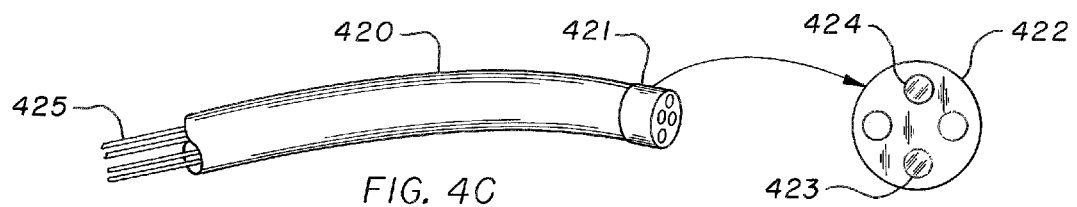
FIG. 4C illustrates an endoscope according to an embodiment of the present invention.

FIGS. 4A-C illustrate variations of endoscopes according to embodiments of the present invention. Referring to FIG. 4A, endoscope 400 may be used to examine interiors of internal human organs/cavities and generate full-field, 3-D representations of the organs/cavities. Endoscope 400 may include a catheter section 401, a distal end 402, a camera 404 (similar to camera 110 of FIG. 1), and a radiation source 403 (similar to radiation source 112 of FIG. 1). The camera 404 and radiation source 403 may be connected to the catheter section 401 on one end of the catheter section 401 and the distal end 402 may be connected to the catheter section 401 on another end of the catheter section 401. In other embodiments, the camera 404 and radiation source 403 may both be located at the end of catheter section 401 opposite distal end 402, the camera 404 and radiation source 403 may both be located at the end of catheter section 401 at distal end 402, or the camera 404 and radiation source 403 may be located at opposite ends of catheter section 401.

Catheter section 401 may be a flexible shaft and may include a number of channels (not shown) which may facilitate an examination of a patient's body. The channels in the catheter section 401 may run from one end of the catheter 401 to another end to allow transmission of data between camera 404/radiation source 403 and distal end 402 (described in further detail below). The channels may permit a physician to engage in remote operations such as transmission of images captured by the distal end 402, providing radiation generated by the radiation source 403 to distal end 402, irrigation for washing and removing debris from distal end 402 (using air/water pathway 407 and suction pathway 408), and introduction of medical instruments into a patient (via instrument pathway 409).

Operation of an endoscope according to an embodiment of the present invention will now be described with respect to FIGS. 4A and 4B. FIG. 4B illustrates a detailed view of catheter section 401 of endoscope 400 according to an embodiment of the present invention. Cather section 401 may include distal end 402 and a fiber optics bundle 411. Distal end 402 may include a distal tip 410 with projection optics 412 and imaging optics 413. The projections optics 412 and imaging optics 413 may each include a lens to focus the radiation used by the endoscope 400. Lenses may be used to focus radiation, and may include optical lenses, parabolic reflectors, or antennas, for example. Fiber optics bundle 411 may connect radiation source 403 to projection optics 412 to facilitate transmission of electromagnetic radiation from radiation source 403 to projection optics 412. Fiber optics bundle 411 may also connect camera 404 to imaging optics 413 to facilitate transmission of imaging data captured by imaging optics 413 to camera 404.

Endoscope 400 may generate full-field, 3-D representations of internal human organs and cavities using the SSM techniques described above with respect to FIGS. 1-3. During an operation, distal end 402 and catheter shaft 401 may be inserted into a patient and guided to a surface inside the patient's body that is under examination. Once the distal end 402 is properly oriented, the radiation source 403 may transmit a spatial pattern of electromagnetic radiation to projection optics 412 via fiber optics bundle 411. As described above with respect to FIGS. 1-3, the frequency of the electromagnetic radiation may be modified depending on the media (the area between the distal tip 410 and the target surface) the radiation is propagating through. The pattern of electromagnetic radiation may be projected onto the surface under examination by placing a slide or grating (not shown) with a desired pattern between the radiation source 403 and the fiber optics bundle 411 in the catheter section 401. The pattern of electromagnetic radiation may propagate through the fiber optics bundle 411, exit through projection optics 412 at the distal tip 410, and project onto the target surface.

The spatial radiation signals may reflect from the target surface back to the distal tip 410 and imaging optics 413 may capture the reflected signals (which are modulated by interaction with the surface). The captured reflection images may be transmitted from imaging optics 413 to camera 404 via fiber optics bundle 411 and subsequently transmitted to a controller system (not shown, but similar to controller system 106 of FIG. 1). The controller system may use existing information regarding various signal parameters to isolate the content of the reflected spatial signal that contains the 3-D shape information. The shape information may be used to mathematically reconstruct the 3-D shape of target surface.

Moreover, endoscope 400 may be used to construct full-field surface maps of long passageways in a patient's body (e.g., gastrointestinal passageways) by moving the endoscope 400 through a given passageway. While endoscope 400 is being guided through a given passageway, continuous full-field surface maps may be generated by stitching together the 3-D data gathered during each video frame captured by camera 404. The 3-D data may be stitched together using algorithms known in the art implemented in software, hardware, or a combination of software and hardware. In this manner, an accurate 3-D model of the cavity in which the device is traveling may be constantly digitally developed and recorded. Thus, embodiments of the present invention may provide a continuous real-time, 3-D representation of the interior of a patient's gastrointestinal passageways. Such methods may also be used for other internal organs that may not be captured by a stationary endoscope.

FIG. 4C illustrates another embodiment of a catheter section 420 with a distal end 421 and electrical and data leads 425 in accordance with the present invention. Distal end 421 may include a distal tip 422 with imaging optics 424 (similar to imaging optics 413 in FIG. 4B) and electromagnetic radiation emitter 423. Electromagnetic radiation emitter 423 may be molded onto distal tip 422 and may project the spatial radiation signals (similar to the signals described above with respect to FIGS. 1-4B). Emitter 423 may contain a lamp, a pattern slide, and a lens (not shown, but described in FIG. 5 below) and may project a spatial pattern onto a target surface when power is provided to it via electrical and data leads 425. Thus, there is no need for an external electromagnetic radiation source (similar to source 403 in FIG. 4) because emitter 423 may be capable of locally generating radiation patterns and projecting them onto target surfaces.

Catheter section 420 may be utilized alone, integrated into, or passed through the working lumen of an endoscopic device (similar to endoscope 400 of FIG. 4A, but possibly without the radiation source 403) and may utilize the SSM techniques described above. During operation, emitter 423 may receive power via electrical and data leads 425 and subsequently project a spatial electromagnetic radiation pattern onto a target surface according to a spatial signal modulation algorithm. The frequency of the electromagnetic radiation used to project the spatial pattern may be modified depending on the media which the radiation is propagating through (as previously described).

The spatial radiation signals may reflect from the target surface back to the distal tip 422 and imaging optics 424 may capture the reflected signals (which are modulated by interaction with the surface). The captured reflection images may be transmitted from imaging optics 424 to a camera (not shown, but similar to camera 404 in FIG. 4A) via electrical and data leads 425 and subsequently transmitted to a controller system (not shown, but similar to controller system 106 of FIG. 1). The controller system may use existing information regarding various signal parameters to isolate the content of the reflected spatial signal that contains the 3-D shape information. The shape information may be used to mathematically reconstruct the 3-D shape of target surface.

Embodiments of the present invention integrating the catheter section 420 with distal end 421 into an endoscopic device may also be used to construct full-field surface maps of long passageways in a patient's body (e.g., gastrointestinal passageways) by moving the endoscope through a given passageway (similar to the embodiment described with respect to FIGS. 4A-B). While the endoscope is being guided through a given passageway, continuous full-field surface maps may be generated by stitching together the 3-D information calculated from information contained in each video frame captured by the camera.

Figure 5:
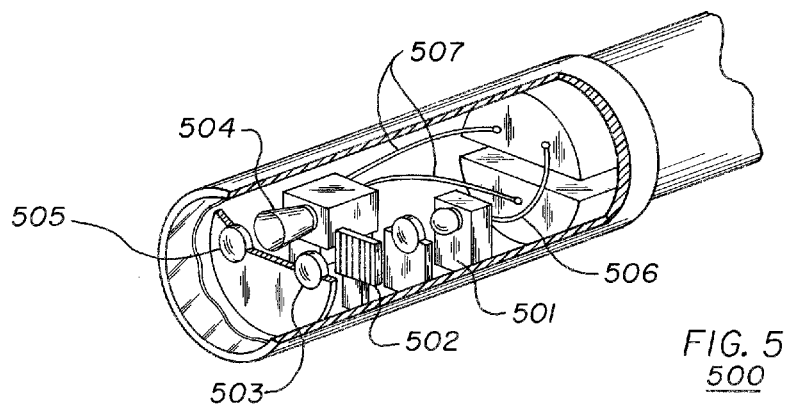
FIG. 5 illustrates a distal end according to an embodiment of the present invention.

FIG. 5 illustrates a detailed, cross-sectional view of a distal end 500 that may be integrated with an endoscope described above with respect to FIG. 4C according to an embodiment of the present invention. Distal end 500 may include a lamp 501, a pattern slide 502, an illumination lens 503, an imaging sensor 504, and an imaging lens 505.

Lamp 501, pattern slide 502, and illumination lens 503 may form an electromagnetic radiation emitter (not specifically labeled, but similar to emitter 423 in FIG. 4C) capable of projecting patterns of radiation onto a target surface according to a spatial signal modulation algorithm. The frequency of the electromagnetic radiation used to project the spatial pattern may be modified depending on the media which the radiation is propagating through (as previously described). During operation, lamp 501 may receive power from a power source (not shown) via electrical lead 506 and project electromagnetic radiation through pattern slide 502 and illumination lens 503 onto a target surface.

The spatial radiation signals may reflect from the target surface back to the distal end 500 through imaging lens 505, and imaging sensor 504 may capture the reflected signals (which are modulated by interaction with the surface). The captured reflection images may be transmitted from imaging sensor 504 via data leads 507 to a controller system (not shown, but similar to controller system 106 of FIG. 1). The controller system may use existing information regarding various signal parameters to isolate the content of the reflected spatial signal that contains the 3-D shape information. The shape information may be used to mathematically reconstruct the 3-D shape of target surface.

Figure 6:
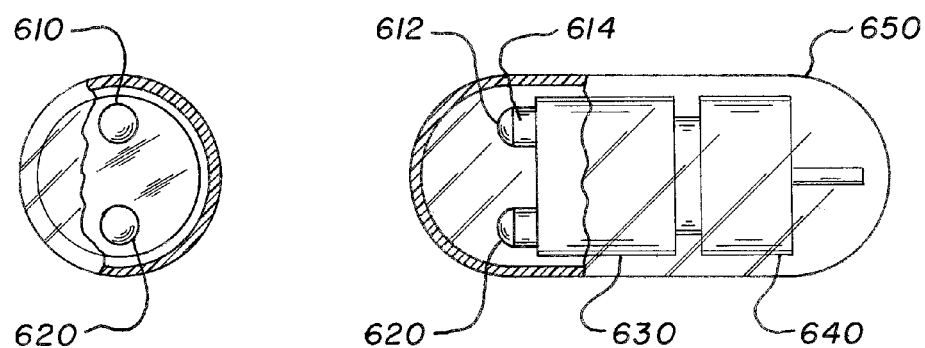
FIG. 6 illustrates a capsule according to an embodiment of the present invention.

FIG. 6 illustrates an endoscopic capsule 600 according to an embodiment of the present invention. FIG. 6 includes a cross-sectional view (on the left) and an overhead view (to the right) of capsule 600. Capsule 600 may be a small vitamin pill sized capsule that is capable of being ingested by a patient. The capsule 600 may implement the SSM techniques described above to generate full-field, 3-D representations of surfaces of a human digestive tract that are difficult to reach through traditional endoscopic examination.

Capsule 600 may include an imaging package 610, an electromagnetic radiation package 620, power supply and electronics 630, a wireless transmitter 640, and a transparent protective cover 650. The cover 650 may be an outer shell capable of protecting the devices in capsule 600 while it is flowing through the digestive tract of a patient. Imaging package 610 may include imaging optics 612 (e.g., a lens) and imaging sensor 614.

Capsule 600 may operate in a similar fashion to the embodiments described above, however, capsule 600 may be powered locally via power supply and electronics 630, which may include a battery, for example. Moreover, capsule 600 may transmit captured image data to an image processing module (not shown, but similar to controller system 106 of FIG. 1) located external to a patient's body using wireless transmitter 640. An antenna module (not shown) may be placed on the skin of the patient to facilitate data transmission from the capsule to the image processing module.

During operation, a patient may ingest capsule 600, which travels through the patient's digestive tract for measurement purposes. While capsule 600 is traveling through the patient's digestive tract, electromagnetic radiation package 620 (which may include an emitter that is similar to the electromagnetic radiation emitter 423 of FIG. 4C) may be powered by power supply and electronics 630 to constantly project spatial electromagnetic radiation patterns on surfaces in its path. The frequency of the electromagnetic radiation used to project the spatial pattern may be modified depending on the media (e.g., visible frequency transparent gases and clear fluids) which the radiation is propagating through (as previously described).

The spatial radiation signals may reflect from the target surface back to the imaging optics (the signals may be modulated by interaction with the surface). Image sensor 614 may capture the reflected images and transmit them, via wireless interface 640, from the capsule 600 to an image processing module (now shown, but similar to controller system 106 of FIG. 1). The image processing module may use existing information regarding various signal parameters to isolate the content of the reflected spatial signal that contains the 3-D shape information. The shape information may be used to mathematically reconstruct the 3-D shape of the target surface.

Reflection images captured by capsule 600 may be used to construct full-field surface maps of a patient's digestive tract as the capsule 600 is traveling in the tract by stitching together the 3-D data gathered during each video frame captured by image sensor 614. In this manner, an accurate 3-D model of the cavity in which the device is traveling may be constantly digitally developed and recorded. Capsule 600 may be generally moved along involuntarily by peristalsis or selectively propelled/guided electromagnetically.

Figure 7A:
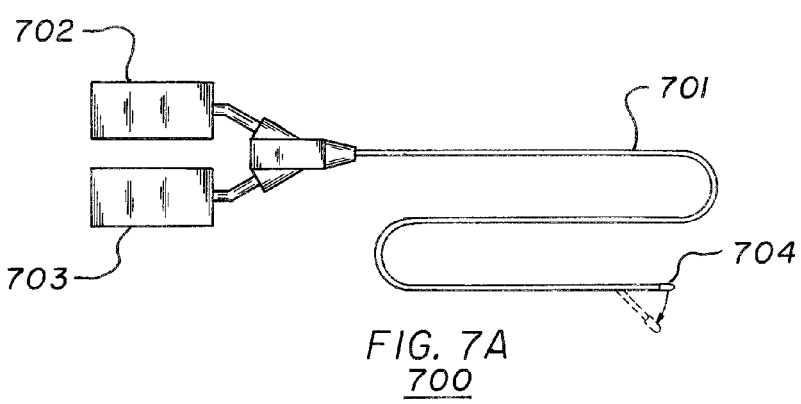
FIG. 7A illustrates a catheterization probe according to an embodiment of the present invention.
Figure 7B:
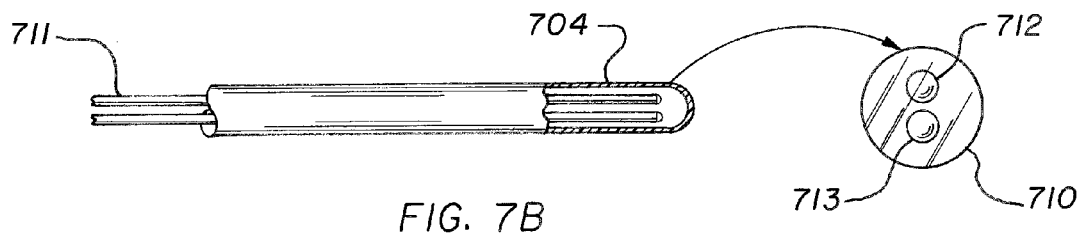
FIG. 7B illustrates a catheterization probe according to an embodiment of the present invention.

FIGS. 7A and 7B illustrate two views of a catheterization probe 700 according to an embodiment of the present invention. The probe 700 may be employed during a catheterization procedure to quantitatively examine structures during normal function or, for example, to detect and measure plaques and blockages in the coronary arteries. The catheterization probe 700 may include a catheter section 701, a radiation source 702 (similar to radiation source 403 of FIG. 4A), a radiation sensor 703, and a distal end 704. The radiation source 702 and the radiation sensor 703 may be connected to the catheter section 701 on one end of the catheter section 701, and the distal end 704 may be connected to the catheter section 701 on the other end of the catheter section 701. In other embodiments, radiation source 702 and the radiation sensor 703 may both be located at the end of catheter section 701 opposite distal end 704, radiation source 702 and the radiation sensor 703 may both be located at the end of catheter section 701 at distal end 704, or radiation source 702 and the radiation sensor 703 may be located at opposite ends of catheter section 701.

Catheter section 701 may be a flexible shaft and may include a fiber optics bundle 711 and a distal end 704. The distal end 704 may include a distal tip 710 with projections optics 712 and imaging optics 713. The projections optics 712 and imaging optics 713 may each include a lens to focus the radiation used by the probe 700. Fiber optics bundle 711 may connect radiation source 702 to the projection optics 712 to facilitate transmission of electromagnetic radiation from radiation source 702 to projection optics 712. Fiber optics bundle 711 may also connect radiation sensor 703 to imaging optics 713 to facilitate transmission of imaging data captured by imaging optics 713 to radiation sensor 703.

Catheterization probe 700 may generate full-field, 3-D representations of vascular anatomy such as heart valves, coronary arteries, or peripheral vasculature using the SSM techniques described above with respect to FIGS. 1-6. During a procedure the long, thin, and flexible shaft of the catheter section 701 may be introduced into a blood vessel and threaded into the target vessels of the heart. The probe 700 may have sufficient torsional rigidity and a deflectable portion at the distal end 704 (show in FIG. 7A) to facilitate torque steering as it is advanced within a cardiovascular environment.

Once the distal end 704 is properly oriented, the radiation source 702 may transmit a spatial pattern of electromagnetic radiation to projection optics 712 via fiber optics bundle 711. As described above with respect to FIGS. 1-6, the frequency of the electromagnetic radiation may be modified depending on the media (the area between the distal tip 710 and the target surface) the radiation is propagating through. The pattern of electromagnetic radiation may be projected onto the surface under examination by placing a slide or grating (not shown) with a desired pattern between the radiation source 702 and the fiber optics bundle 711 in the catheter section 701. The pattern of electromagnetic radiation may propagate through the fiber optics bundle 711, exit through projection optics 712 at the distal tip 710, and project onto the target surface.

The spatial radiation signals may reflect from the target surface back to the distal tip 710 and imaging optics 713 may capture the reflected signals (which are modulated by interaction with the surface). The captured reflection images may be transmitted from imaging optics 713 to radiation sensor 703 via fiber optics bundle 711 and subsequently transmitted to a controller system (not shown, but similar to controller system 106 of FIG. 1). The controller system may use existing information regarding various signal parameters to isolate the content of the reflected spatial signal that contains the 3-D shape information. The shape information may be used to mathematically reconstruct the 3-D shape of target surface.

In this manner, full field digital 3-D surface maps of cardiac cavities may be continuously generated by the measurement package (projection optics 712 and imaging optics 713) located at the distal tip 710 of the probe 700. These computer generated maps combine to form a virtual environment of the interior surface of the cavity under study. This information may be presented on a display device, either locally to the attending operating room staff, or transmitted remotely, creating a telepresence for diagnosis by an expert located remotely from the patient. The real-time 3-D model information may be used as a navigational aid within the vessel, tracking and recording progress and surface structures. Once within the vascular or cardiac structures, the distal tip 710 may be navigated to the area of interest and may provide accurate, direct, and quantitative 3-D observation of a functioning anatomy.

Embodiments of the present invention described above provide devices and methods to generate accurate, high-speed 3-D surface representations. By carefully varying the frequency of the radiation projected onto target surfaces, physicians may be able to see through media that were previously considered opaque. Tailoring emitter-sensor packages to specific frequencies depending on the media the radiation is traveling through allows reproduction of 3-D surfaces both internal and external to the human body.

Moreover, integrating the SSM techniques described above with medical devices such as probes, endoscopes, catheters, or capsules may enable physicians to generate accurate full-field, 3-D representations of surfaces that were previously very difficult to produce. The medical applications of in-vivo topometric data are innumerable. Internal real-time 3-D sensing applied through endoscopic or catheter based inspection of gastrointestinal, cardiovascular, or bronchial passageways may assist detection of anomalous structures, constrictions, or growths. Devices and methods in accordance with the embodiments of the present invention described above may be invaluable for virtual biopsies and early detection in oncology as many cancers may originate on surfaces of the internal anatomy. Catheter based, quantifiable 3-D mapping of plaque strictures in coronary arteries may allow for better diagnosis of heart disease and placement of stents or other appliances. There are numerous other medical applications for the techniques and devices described above.

Those skilled in the art may appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

I claim:

1. A system for providing a continuous, full-field, three-dimensional representation of a target surface inside a human body, the system comprising:
    a catheter, the catheter having a proximal end and a distal end adapted to be inserted into the human body and guided to the target surface inside the human body;
    projection components for projecting infrared radiation onto the target surface in a projected pattern, the projection components comprising an infrared radiation emitter connected to the proximal end of the catheter, a projection lens located at the distal end of the catheter, fiber optics capable of transmitting the infrared radiation from the infrared radiation emitter to the projection lens, and a grating positioned between the infrared radiation emitter and the projection lens, wherein infrared radiation that is emitted from the infrared radiation emitter and that passes through the grating and the projection lens is projected onto the target surface in the projected pattern;
    imaging components for capturing a plurality of successive images of infrared radiation reflected from the target surface, the imaging components comprising an imaging lens located at the distal end of the catheter, an infrared image sensor connected to the proximal end of the catheter and configured to capture image data corresponding to the plurality of successive images of infrared radiation reflected from the target surface, and fiber optics capable of transmitting infrared radiation from the imaging lens to the infrared image sensor;
    an image processing module configured to receive the captured image data from the infrared image sensor and to calculate a full-field, three-dimensional representation of the target surface for each image of the plurality of successive images of infrared radiation reflected from the target surface using the captured image data and a spatial signal modulation algorithm, wherein the images comprise successive reflections of the projected pattern modulated by the target surface, and wherein the images differ from each other due to relative movement between the catheter and the target surface, resulting in a plurality of successive full-field, three-dimensional representations of the target surface; and
    a display device configured to display the plurality of successive full-field, three-dimensional representations of the target surface.

2. The system of claim 1 further comprising one or more of:
    an instrument port; and
    an irrigation module.

3. The system of claim 2, wherein the irrigation module comprises:
    a channel to provide liquid or air; and
    a suction channel to remove liquid or air.

4. A method for providing a continuous, full-field, three-dimensional representation of a target surface inside a human body, the method comprising:
    projecting infrared radiation onto the target surface inside the human body in a projected pattern using projection components, the projection components comprising an infrared radiation emitter, a projection lens located at the distal end of a catheter wherein the distal end of the catheter is positioned inside the human body, fiber optics capable of transmitting the infrared radiation from the infrared radiation emitter to the projection lens, and a grating positioned between the infrared radiation emitter and the projection lens, wherein infrared radiation that is emitted from the infrared radiation emitter and that passes through the grating and the projection lens is projected onto the target surface in the projected pattern;
    capturing, by an infrared image sensor, image data corresponding to a plurality of successive images of infrared radiation reflected from the target surface, wherein the images comprise successive reflections of the projected pattern modulated by the target surface, and wherein the images differ from each other due to relative movement between the catheter and the target surface;
    providing the captured image data to an image processing module;
    calculating, by a processor of the image processing module, a full-field, three-dimensional representation of the target surface for each image of the plurality of successive images of infrared radiation reflected from the target surface using the captured image data and a spatial signal modulation algorithm, resulting in a plurality of successive full-field, three-dimensional representations of the target surface; and
    displaying the plurality of successive full-field, three-dimensional representations of the target surface on a display device.

5. The method of claim 4, wherein the infrared radiation emitter and the infrared image sensor are integrated into a system for providing a continuous, full-field, three-dimensional representation of a target surface, the system comprising one or more of:
   an instrument port; and
   an irrigation module.

6. The method of claim 5, wherein the irrigation module comprises:
   a channel to provide liquid or air; and
   a suction channel to remove liquid or air.

* * * * *